United States Patent [19]

Aoki et al.

[11] Patent Number: 5,044,764
[45] Date of Patent: Sep. 3, 1991

[54] METHOD AND APPARATUS FOR FLUID STATE DETERMINATION

[75] Inventors: Kazuichi Aoki; Yukihiro Saiki, both of Saitama, Japan

[73] Assignee: Snow Brand Milk Products Co., Ltd., Hokkaido, Japan

[21] Appl. No.: 486,943

[22] Filed: Mar. 1, 1990

[30] Foreign Application Priority Data

Mar. 8, 1989 [JP] Japan ................................. 1-55648

[51] Int. Cl.⁵ ...................... G01N 25/02; G01N 25/20; G01F 23/22
[52] U.S. Cl. ................................. 374/16; 374/54; 374/11; 374/10; 73/295
[58] Field of Search .................. 374/10, 11, 16, 54; 73/295

[56] References Cited

U.S. PATENT DOCUMENTS

| 3,279,252 | 10/1966 | Barlow | 73/295 |
|---|---|---|---|
| 3,324,722 | 6/1967 | Reicks | 73/295 |
| 3,360,990 | 1/1968 | Greene et al. | 73/295 |
| 3,614,387 | 10/1971 | Wrob et al. | 374/166 |
| 3,653,262 | 4/1972 | Ehrenfried et al. | 374/142 |
| 3,905,243 | 9/1975 | Goldfuss | 73/295 |
| 4,423,629 | 1/1984 | Arb et al. | 73/295 |
| 4,439,396 | 3/1984 | Rolstad | 374/10 |
| 4,590,797 | 5/1986 | Beaubatie et al. | 73/295 |
| 4,592,230 | 6/1986 | Waring et al. | 73/295 |
| 4,603,580 | 8/1986 | Waring | 73/295 |
| 4,741,209 | 5/1988 | McCulloch | 73/295 |
| 4,762,427 | 8/1988 | Hori et al. | 374/16 |
| 4,785,665 | 11/1988 | McCulloch | 73/295 |
| 4,805,454 | 2/1989 | LeVert | 73/295 |
| 4,859,076 | 8/1989 | Twerdochlib | 374/10 |

FOREIGN PATENT DOCUMENTS

| 1959041 | 5/1971 | Fed. Rep. of Germany | 73/295 |
|---|---|---|---|
| 0124019 | 9/1980 | Japan | 73/295 |
| 0006116 | 1/1981 | Japan | 73/295 |
| 0158522 | 9/1982 | Japan | 73/295 |
| 0673858 | 7/1979 | U.S.S.R. | 73/295 |
| 0381811 | 10/1932 | United Kingdom | 73/295 |

Primary Examiner—William A. Cuchlinski, Jr.
Assistant Examiner—Diego F. F. Gutierrez
Attorney, Agent, or Firm—Griffin Branigan & Butler

[57] ABSTRACT

A sensor comprising a heating element and a temperature detecting element used to measure a temperature of the heating element are both held out of contact with each other within a sensor protecting tube. For fluid exhibiting slow changes in its state as time elapses, a fluid state is measured on the basis of a differential temperature between temperatures prior to and during heating of the heating element. For the fluid exhibiting rapid changes in its state as time elapses, the sensor is caused to generate heat while the temperature of this sensor is measured, and a separate temperature measuring sensor measures the temperature of the fluid. The fluid state is determined on the basis of the differential temperature between the temperatures of the sensor and the temperatures of the fluid.

7 Claims, 2 Drawing Sheets

METHOD AND APPARATUS FOR FLUID STATE DETERMINATION

BACKGROUND OF THE INVENTION

This invention relates to a measuring sensor for fluid state determination and a method for measurement using such sensor, and is applicable particularly to the temperature measurement conducted to evaluate viscosity or physical properties of given fluid as well as to the measurement conducted to localize a fluid level.

It should be understood that the term "fluid" used herein includes substance in the form of gas, liquid, solid or mixtures of two or more thereof and the term "state" used herein includes not only stationary or flowing state of given fluid but also a state of this fluid in which composition, phase or temperature thereof is steady or variable with the passage of time.

Various methods for measuring a state of given fluid have already been proposed and the inventors also have disclosed methods for measuring a fluid state using metallic thin wire by hot wire method, for example, in Japanese patent application Disclosure Gazettes No. 1985-152943; 1987-27622; 1987-40246; and 1987-56849. According to these prior arts, changes of physicals properties or the like occurring in given fluid are thermally measured on the basis of change in temperature with the passage of time occurring when the metallic thin wire placed within the fluid is applied with electric current and thereby the state of the fluid is determined.

Of the sensors used in such measurement, the sensor disclosed in Japanese patent application Disclosure Gazette No. 1987-56846 (U.S. Pat. No. 4,762,427) comprises metallic thin wire wound around a holding shaft coated with electrical insulator, this assembly as a whole being coated with electrical insulator, so as to be used with said method.

The method disclosed in Japanese patent application Disclosure Gazette No. 1987-185146 employs, in addition to a measuring sensor, alone, used to measure a fluid temperature, an electrical heating sensor so that the state of the fluid may be determined more accurately on the basis of a differential temperature given by these two sensors.

Usually, means such as resistance thermometer bulb, thermistor, thermocouple and radiation thermometer have been utilized as temperature detecting means for measurement of fluid.

The sensor used in the measuring methods or the like of prior art which have been proposed by the inventors comprises, as mentioned above, the metallic thin wire wound on the shaft and is certainly advantageous in that a length of said metallic thin wire may be dimensioned to be several times of the sensor's own length and thereby an electric resistance thereof may be increased so as to obtain a high heating value from a small current value. Such sensor is advantageous also in that the sensor itself cannot be easily damaged or bent.

However, such prior art is disadvantageous in that when the metallic thin wire is spirally bent while being wound on the shaft a stress/strain is developed in said metallic thin wire and an annealing process is necessary to relieve such stress/strain significantly changes a resistance value with respect to the initial value.

Since it is difficult to presume a degree of this change in the resistance value, it is also difficult to obtain the sensor presenting a desired resistance value. Even when the sensors are mass-produced, there is provided no intersensor compatibility unless the sensors are individually calibrated. The characteristic calibration of individual sensors has been disclosed by the inventors in Japanese patent application Disclosure Gazette No. 1987-51520 (U.S. Pat. No. 4,832,504). However, such characteristic calibration of individual sensors is a time-consuming operation.

To minimize bending of the metallic thin wire, the inventors has proposed an improved sensor in Japanese patent application Disclosure Gazette No. 1989-44838, in accordance with which the metallic thin wire is rectilineally arranged in the longitudinal direction and bent only at opposite ends so that a stress/strain developed in the metallic thin wire may be substantially reduced. However, this invention requires not only a high technique for manufacturing but also a high precision analyzer such as a computer for high precision measurement.

SUMMARY OF THE INVENTION

Accordingly, a principal object of the invention is to measure a state of given fluid with a precision which is slightly lower than the precision expected to be achieved by using the electrical heating type sensor of prior art but practically acceptable, utilizing a simplified manufacturing technique, e.g., a conventional digital thermometric mechanism.

The object as set forth above is achieved, according to the invention, by a measuring sensor used to measure a state of fluid, said measuring sensor comprising a sensor protecting tube, a heating element and a temperature detecting element to measure a temperature of said heating element, with both being contained within said protecting tube but such that said temperature detecting element is maintained out of contact with said heating element.

It should be understood that thermally good conductive but electrically insulative material may be interposed between the heating element and the temperature detecting element to keep these elements out of contact with each other and thereby a further preferable sensor may be obtained.

The measuring sensor of the invention provides an effect as follows:

The measuring sensor of the invention comprises, as has been mentioned above, the temperature detecting element and the heating element which are separately provided and held out of contact with each other by the electcial insulator having good thermal conductivity, and wherein the heating element is not always required to be provided in a spiral configuration and therefore can be obtained by a relatively simplified manufacturing technique. Additionally, the durability of the measuring sensor as a whole is enhanced by the feature of the invention that the temperature detecting element and the heating element can be contained within the protecting tube. Furthermore, the measuring sensor of the invention has a sufficiently rapid responsiveness to achieve the desired measurement so far as the measuring sensor is used for measurement of the fluid state and requires no high precision of manufacture, since a temperature of the heating element is measured by the temperature detecting element. The temperature detecting element may be replaced by any suitable commercially available thermometric device. Moreover, the measuring sensor of the invention can be constructed in a compact handy type which is convenient for handling.

The measuring sensor of the invention is useful not only as measuring means for the fluid state but also as a universal temperature sensor. For the fluid, such as a sampled fluid, exhibiting no change in its state with the passage of time, the invention enable a single measuring sensor to determine a differential temperature.

The object as set forth above is achieved, in accordance with the invention, also by a method for measurement of fluid state on the basis of a differential temperature determined before and during heating of the heating element, utilizing said sensor.

The object as set forth above is also achieved by a method for measurement of fluid state on the basis of a differential value between two temperature values determined by said sensor and an other general temperature detecting sensor both placed in the fluid during heating of said sensor.

With the method of the invention as mentioned above, if the fluid state exhibits no change as the time elapses, said single measuring sensor comprising the heating element and the temperature detecting element adapted to measure a temperature of said heating element may be used to measure the fluid state on the basis of the differential temperature between the temperature obtained by said temperature detecting element before heating of said heating element as the temperature of the fluid and the temperature obtained by said temperature detecting element during heating of said heating element as the temperature of the sensor.

For the fluid state exhibiting a change as the time elapses, on the other hand, a general temperature detecting sensor such as a resistance thermometer bulb may be used with the sensor of the invention to measure such fluid state.

BRIEF DESCRIPTION OF THE DRAWINGS

The above and other objects of the invention will be seen by reference to the description taken in connection with the accompanying drawings, in which.

DETAILED DESCRIPTION OF THE INVENTION

Figure 1:
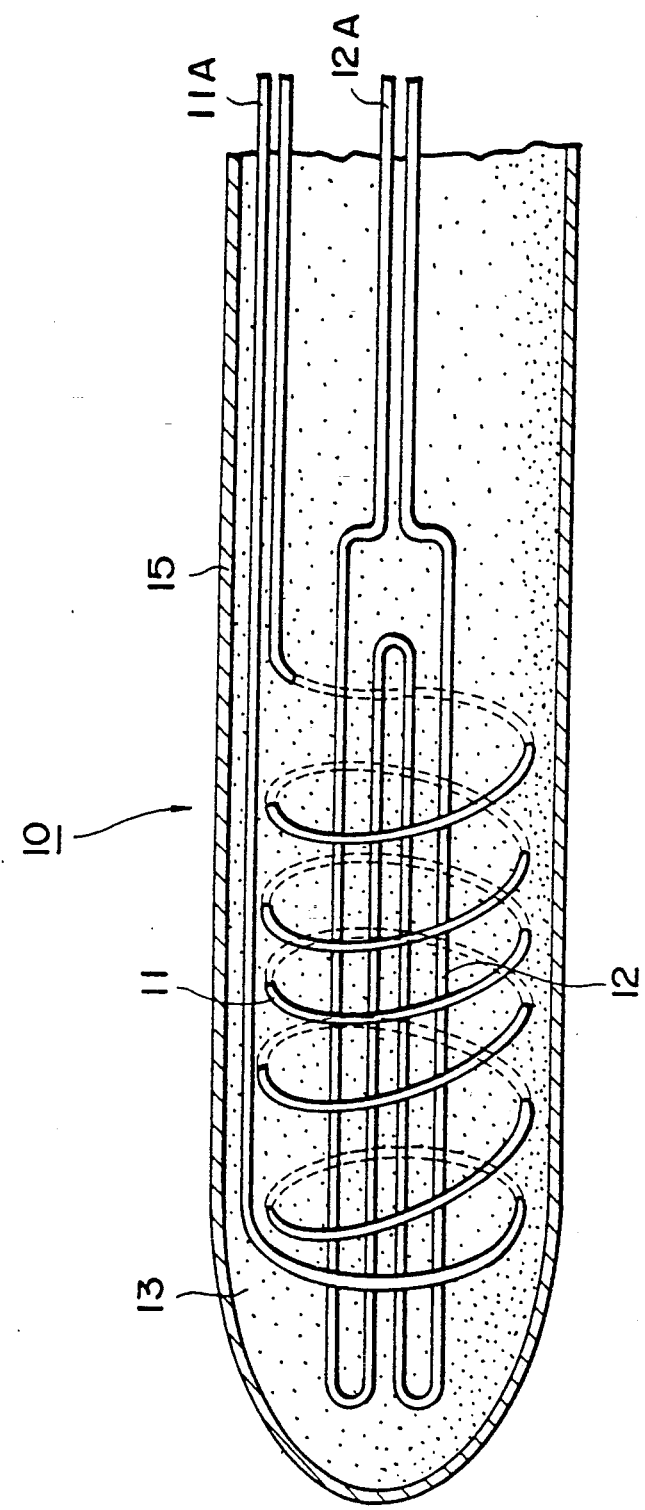
FIG. 1 is a sectional view of a measuring sensor constructed in accordance with the invention.

The electrical heating type sensor previously proposed by the inventors has been very useful in the field of chemical and pharmaceutical industries or the like in which a high precision is required. However, the precision of such a degree as to measure slight changes of fluid by the electrical heating sensor of prior art is usually unnecessary for fluid state measurement or the like in a raw material storage equipment or during a primary processing, for example, during the raw material storage or any process prior to the actual manufacturing process for general foods, i.e. in such fields where the fluid exhibits rapid changes in its state. It should be understood, however, that, even in such food industry, a careful consideration must be undertaken so as to obtain a measurement free from any error possibly caused by various conditions of measurement such as speediness thereof.

The present invention was made in view of these requirements and principally utilizes the method of well known art in that a differential value between the fluid temperature and the sensor temperature is measured to determine the fluid state. According to the invention, however, there is provided a relatively simplified structure where the sensor comprises the heating element and the temperature detecting element used to measure the temperature of this heating element so that the desired measurement can be achieved by used of the single sensor, except when a pair of sensor must be used for the fluid exhibiting a change in its state as the time elapses, without use of any high degree analyzer.

In other words, the inventors of the invention have formerly disclosed a sensor which not only generates heat, but also measures the temperature of the sensor itself. On the contrary, the sensor of the present invention is provided with a heating element which only generates heat, and a separate temperature detecting element for measurement of the temperature of the heating element. This makes it easier to control the heat generated by the heating element and no calculating equipment and surrounding equipment to calculate the temperture and the like is required. Accordingly, the measurement is managed by a simple controller, and in a consequence, the device itself can be portable.

With the conventional sensor of electrical heating type requiring a pair of sensors, i.e., the measuring sensor provided heating element and the temperature sensor, it has been essential to prevent these two sensors from being affected by each other and to assure a sufficient amount of sample to allow use of the apparatus thus comprising two sensors for effective measurement of sampled fluid or the like.

For example, the sensor disclosed by the inventors in Japanese patent application Disclosure Gazette No. 1987-185146 is adapted to measure a fluid state by the electrical heating method utilizing metallic thin wire, namely, by comparatively measuring the sensor temperature, the fluid temperature and the differential temperature therebetween. The method disclosed mainly herein uses more than two measuring elements respectively for measurement of the heating element temperature and the fluid temperature.

In contrast with this method, the sensor of the invention is adapted to measure the fluid temperature and the sensor temperature by measuring the temperatures of the heating element before and during heating thereof and thereby to determine comprehensive state of the fluid.

In this way, the sensor of the invention is able to measure the fluid state by use of a single sensor and useful particular for the fluid exhibiting not rapid but slow change in its state as the time elapses.

The sensor of the invention thus requires no consideration as has been essential to the conventional sensor of electrical heating type, for example, any countermeasure to prevent a pair of sensors from being affected by each other.

Although, for the fluid exhibiting rapid changes in its state with the passage of time, an additional general temperature detecting sensor must be provided to measure a fluid temperature as is the case with the sensor of prior art, the sensor itself comprising the heating element and the temperature detecting element adapted to measure temperature of this heating element according to the invention is useful not only in the industrial fields requiring no measuring slight changes of fluid with high precision but also have no less durability and rapid responsiveness than the high precise measuring sensor.

Of the electrical heating sensors of prior art, the one disclosed in the previously referred Japanese patent Disclosure Gazette No. 1987-56849 (U.S. Pat. No. 4,762,427) comprises metallic thin wire wound around the electrically insulative holding shaft and then coating-treated, and the one disclosed in the previously referred Japanese patent Disclosure Gazette No. 1989-44838 comprises metallic thin wire inserted into the bore formed through the electrically insulative holding shaft and then secured with use of pulverized ceramic or the like. In either case, high techniques have been necessary to manufacture such sensors. The sensor of the invention, on the contrary, can be inexpensively manufactured by the relatively simplified technique, since, according to the invention, the temperature detecting element and the heating element are separately provided and held by the electrically insulative thermal conductor and electrical conductor out of contact with each other. Additionally, the sensor of the invention requires none of the high precision analyzers which have been necessary for the measuring methods of prior art, and can easily perform the desired measurement utilizing the conventional digital thermometric mechanism.

Now a first embodiment of the sensor constructed according to the invention will be described in reference with FIG. 1. The measuring sensor 10 comprises a spiral heating element 11, a zigzag temperature detecting element 12 is centrally located inside said heating element 11, a good thermal insulator 13 interposed between said heating element 11 and said temperature detecting element 12, and a protecting tube 15 containing therein the assembly. Reference numerals 11A, 12A designate wire leads of said heating element 11 and said temperature detecting element 12, respectively. In operation, assumed that fluid 16 exhibits not rapid but slow change in its state or physical disposition as the time elapses. For example, the sensor 10 is immersed into a reservoir 17 of the fluid 16, as illustrated by FIG. 2, then the heating element 11 is applied with electrical current from a power source 18 for the heating element 11 and a heat output of the element 11 detected by the temperature detecting element 12 and converted by a temperature converter 19 to a corresponding temperature, i.e. the temperature of the sensor. Thus, a temperature of the sensor measured before heating is obtained as a temperature of the fluid and a temperature measured during heating is obtained as a temperature of the sensor itself.

Figure 3:
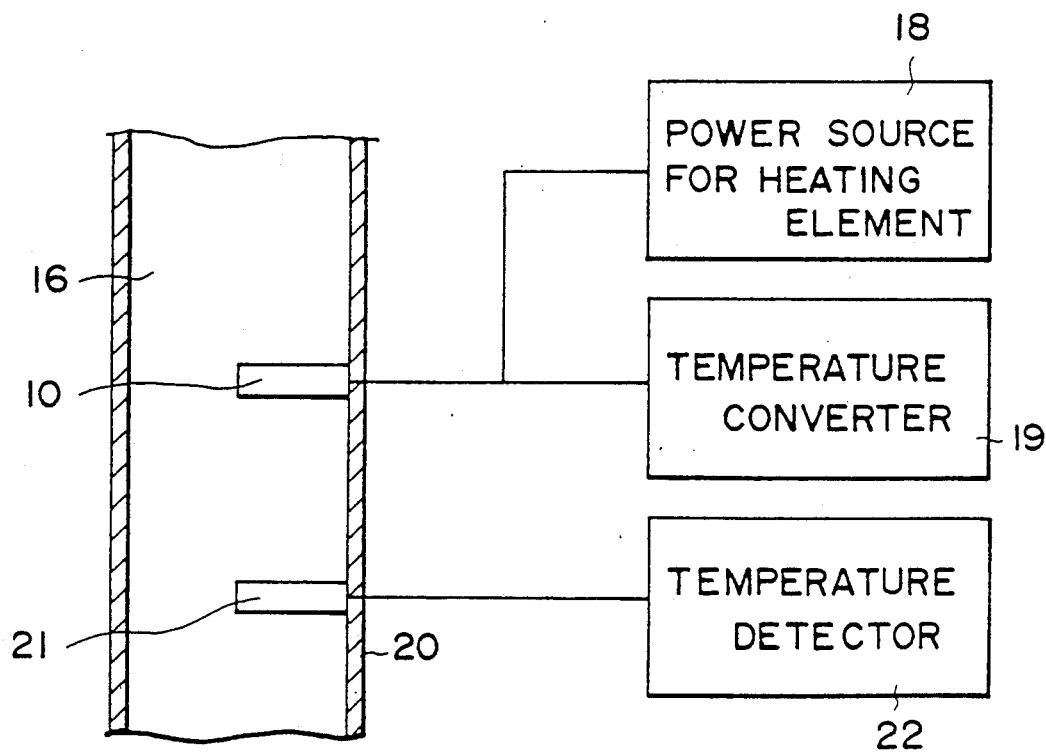
FIG. 3 is a schematic diagram illustrating a manner in which a general temperature detecting sensor is used in combination with the measuring sensor of FIG. 1 to measure the fluid state exhibiting a change as the time elapses.

Then, a second embodiment of the sensor constructed according to the invention with reference to FIG. 3.

FIG. 3 concerns a case in which the fluid state to be measured exhibits rapid changes with the passage of time. Accordingly, this embodiment of the sensor comprises the sensor 10 and a general temperature detecting sensor 21 both fixed within a passage 20 of the fluid. The heating element 11 of the sensor 10 is applied from the power source 18 for the heating element 11 with electric current for heat generation therefrom and an output of this heating element detected by the temperature detecting element 12 is converted by the temperature converter 19 to a corresponding temperature which is read as a temperature of the sensor. A temperature of the fluid 16 is measured by said temperature detecting sensor 21. Reference numeral 22 designates a temperature detector.

In this manner, the temperatures of the fluid and the sensor may be measured to determine a fluid state on the basis of a differential temperature therebetween.

As the electrically insulative good thermal conductor 13, crystalline alumina, ceramic or the like is optimal and preferably powdered to facilitate construction of the sensor. However, it should be understood that said good thermal conductor 13 may be formed from solid material.

It is essential here that said good thermal conductor 13 should be able to hold the heating element and the temperature detecting element out of electrical contact with each other. Furthermore, a distance between these two element is preferably as short as possible in order to assure that the temperature detected by the temperature detecting element substantially approximates the actual temperature of the heating element.

Apparently, this good thermal conductor may be of any material, so far as it is electrically insulative and a precision of measurement is not critical.

Figure 2:
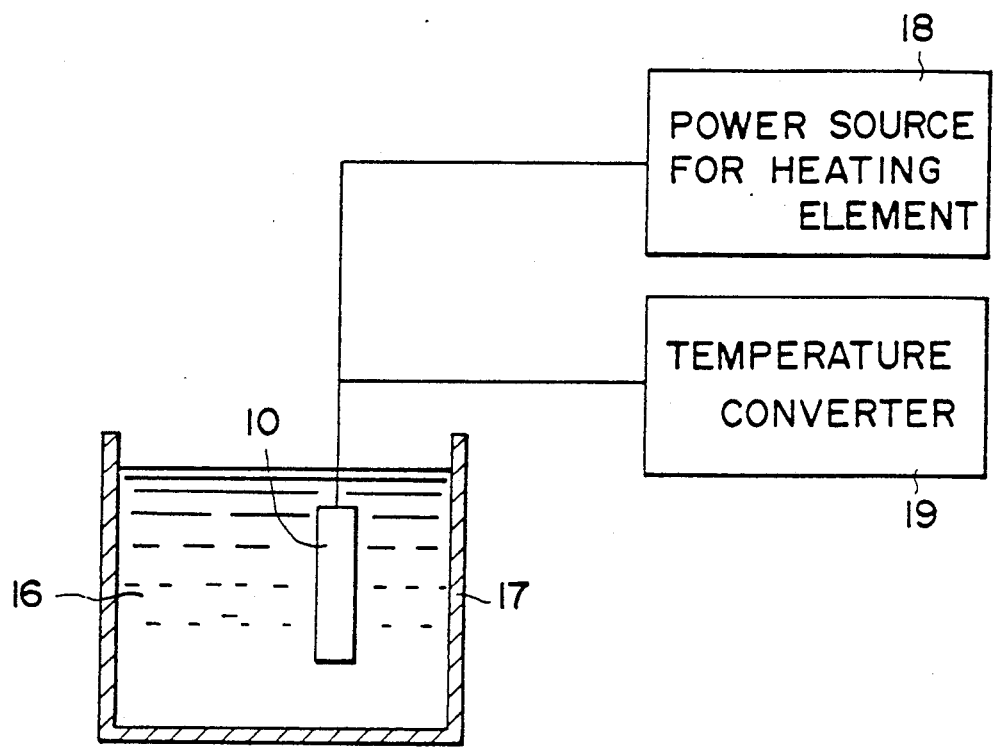
FIG. 2 is a schematic diagram illustrating a manner in which the measuring sensor of FIG. 1 is used for measurement.
Figure 6:
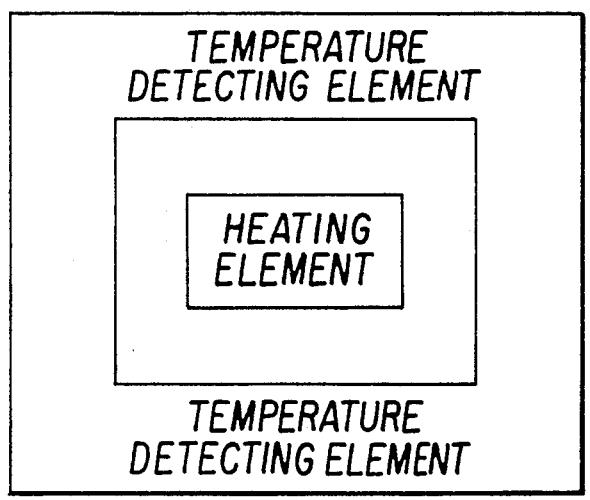
FIG. 6 is a schematic block diagram of an alternative embodiment of the measuring sensor where the temperature detecting element is around the heating element.

The temperature detecting element may be placed around the heating element, as shown in the schematic block diagram of FIG. 6, instead of being placed inside it as in the illustrated embodiment shown in FIG. 1, when it is desired to measure a surface temperature of the measuring sensor. Alternatively, the temperature detecting element may be placed in opposition to the heating element, if desired.

Thus, the relative position of the temperature detecting element and the heating element may be selectively changed depending on the most important output value to be considered in relation to the fluid state.

EXAMPLE A

To localize a fluid level utilizing the sensor of the invention, as disclosed by the inventors in Japanese patent application Disclosure Gazette No. 1987-27622, the sensor may be designed to have an overall length substantially equal to a height of the reservoir and a temperature corresponding to the metallic thin wire temperature $\theta w$ of said prior art may be considered as a temperature detected by the temperature detecting element of the invention, since the level within the reservoir is linearly related to the sensor temperature.

In other words, the temperature detected by the sensor is linearly variable as the level ascends or descends, in proportion to a length of the sensor by which, it is immersed in the fluid.

Accordingly, the temperature measurement may be continuously performed by the temperature detecting element as the heating element, the component of the sensor constructed according to the invention, may be energized for heat generation and the level height changing depending on the temperature may be recorded in relation to respective temperatures so that the level heights can be derived from the corresponding temperature.

Owing to the unique feature of the invention differing from the conventional metallic thin wire that the sensor is placed within the protecting tube, the sensor of the invention is able to resist a shock of some degree possibly occurring, for example, in washing and useful for a wide range of equipment including a large equipment such as a general reservoir.

EXAMPLE B

To determine a fluid state, particularly a coefficient of kinematic viscosity, changing as the time elapses utilizing the sensor of the invention, as illustrated by FIG. 3, one of a plurality of sensing elements may be used as a general fluid temperature detecting element while the other one may be used as the sensor itself to detect two temperatures and a difference therebetween may be continuously or intermittently measured and compared to determine the fluid state, in accordance with the prior art disclosed by the inventors in Japanese patent application Disclosure Gazette No. 1987-185146.

Said differential temperature between two temperatures corresponds to the value $\Delta\theta Wi$ indicated in the above-mentioned Disclosure Gazette and is reflective of the coefficient of kinematic viscosity, so change in $\Delta\theta Wi$ with the passage of time may be plotted in a graphic diagram to determine the change in the coefficient of kinematic viscosity.

In this example, it is important to determine a change in the coefficient of kinematic viscosity and thereby to know a change in the fluid state including the viscosity change therein rather than to determine an exact coefficient value of kinematic viscosity. The relationship between the differential temperature which can be determined by the temperature detecting method of the invention and the coefficient of kinematic viscosity is similar to the relationship which was found by the above-referred prior art, so the sensor of the invention is useful for the fluid exhibiting a significant change in its coefficient of kinematic viscosity.

Figure 4:
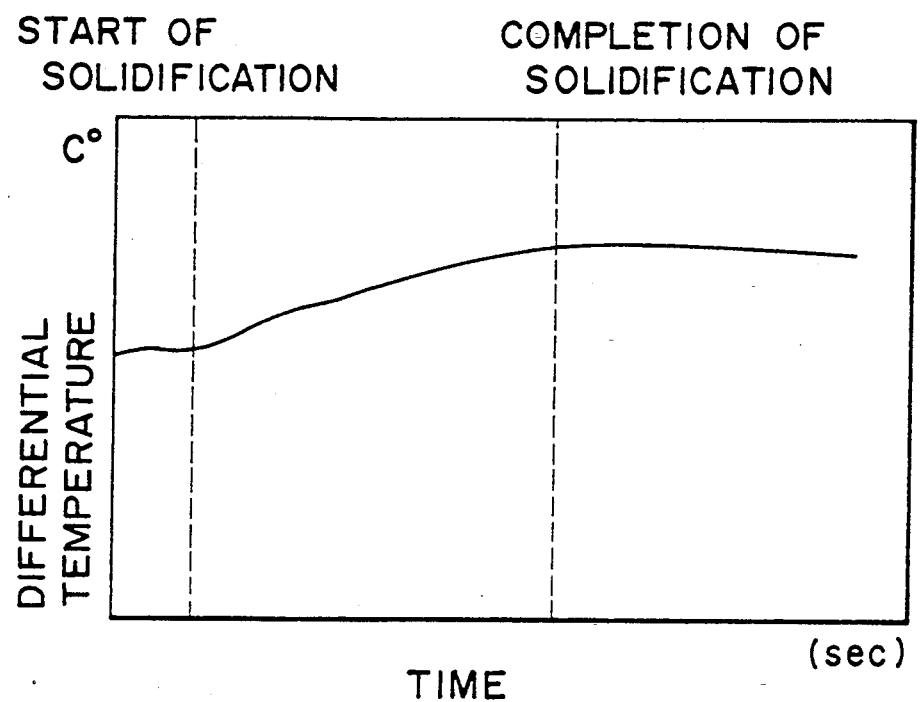
FIGS. 4 and 5 are graphic diagrams showing a process of gelatine solidification as measured by the electrical heating type sensor of prior art and the measuring sensor of the invention, respectively.
Figure 5:
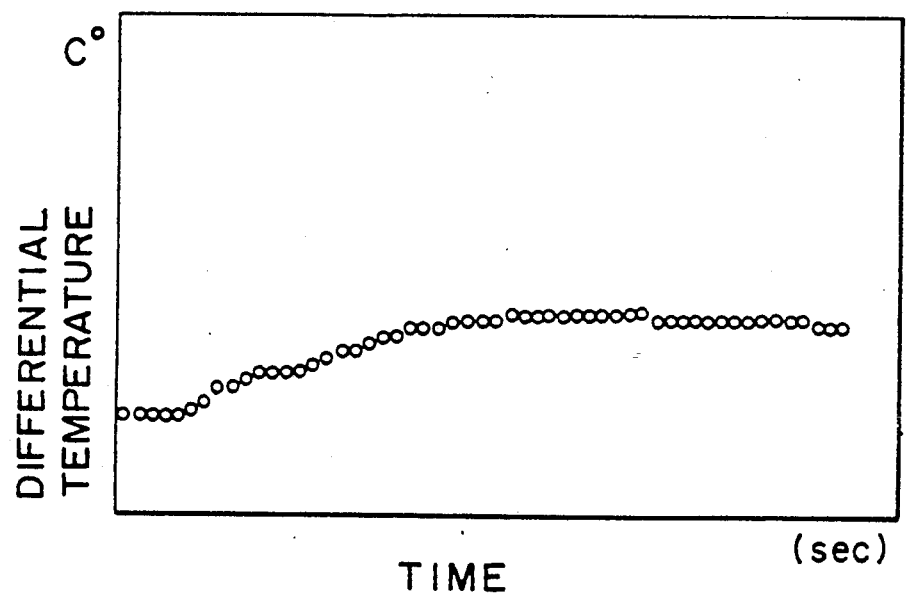

In this regard, according to the method of the present invention an experiment trying to determine solidification of gelatine as the passage of time indicated, as shown by FIG. 5, a result similar to the experimental result (See FIG. 4) conducted according to the measuring method of the above-referred prior art.

With the sensor of the invention, as has previously been described, it is also possible to derive the differential temperature $\Delta\theta W$ from comparison of a temperature measured by the temperature detecting element prior to heating of the sensor and a temperature measured during heating of the heating element being applied with electric current, without use of any separately provided general temperature detecting element.

In this way, the measurement which has usually be accomplished with a pair of sensors according to the prior art can be achieved by the invention with use of a single sensor.

While the invention has been particularly shown and described with reference to preferred embodiment thereof, it will be understood by those skilled in the art that the foregoing and other changes in form and details can be made therein without departing from the sprit and scope of the invention.

What is claimed is:

1. A sensor for measuring the state of a fluid, comprising:
   (a) an elongated outer sheath;
   (b) an elongated electrical heating element disposed substantially along the length of and within said sheath for substantially uniformly heating the sheath along the length thereof and for causing heat to be transferred from said sheath along the length thereof to said fluid at a rate responsive to the state of the fluid along the length of the sheath; and
   (c) an elongated temperature detecting element spaced from said heating element and disposed within said sheath and either (1) generally around the length of said heating element or (2) generally centrally inside the length of said heating element, for measuring the temperature of the heating element by the resistance induced in the temperature detecting element by heat from said heating element.

2. A sensor as recited in claim 1, wherein the heating element and the temperature detecting element are spaced apart by electrically insulative but thermally good conductive material.

3. A sensor as recited in claim 2, wherein the electrically insulative but thermally good conductive material is crystalline alumina or ceramic.

4. A sensor as recited in claim 1, wherein the heating element is spiral shaped.

5. A sensor as recited in claim 1, wherein the temperature detecting element is zigzagged.

6. A method for measurement of a fluid state utilizing the sensor as recited in claim 1, said method comprising the steps of immersing said sensor into the fluid, detecting the temperature of the fluid by use of the sensor prior to heating of the heating element, detecting the temperature of the sensor during heating of the heating element, and measuring the fluid state on the basis of the temperature difference between said temperatures.

7. A method for measurement of a fluid state, said method comprising the steps of placing the sensor as recited in claim 1 in a fluid, causing said sensor to generate heat and detecting the temperature of the sensor, measuring the temperature of the fluid by use of a separate temperature detecting sensor, and measuring the fluid state on the basis of a differential temperature between the temperature of the sensor and the fluid temperature.

* * * * *